(12) United States Patent
Gagnon et al.

(10) Patent No.: US 8,516,636 B2
(45) Date of Patent: Aug. 27, 2013

(54) PATIENT BED FOR PET/MR IMAGING SYSTEMS

(75) Inventors: Daniel Gagnon, Twinsburg, OH (US); Michael A. Morich, Mentor, OH (US); Douglas M. Blakeley, Kirtland, OH (US)

(73) Assignee: Koninklijke Philips N. V., Eindhoven (NL)

( * ) Notice: Subject to any disclaimer, the term of this patent is extended or adjusted under 35 U.S.C. 154(b) by 1390 days.

(21) Appl. No.: 12/195,655

(22) Filed: Aug. 21, 2008

(65) Prior Publication Data
US 2009/0209844 A1  Aug. 20, 2009

Related U.S. Application Data

(63) Continuation of application No. PCT/US2007/081458, filed on Oct. 16, 2007.

(60) Provisional application No. 60/863,637, filed on Oct. 31, 2006.

(51) Int. Cl.
*A61B 6/04* (2006.01)

(52) U.S. Cl.
USPC ......... 5/601; 5/600; 5/611; 600/300; 600/411

(58) Field of Classification Search
USPC ................. 5/600–601, 611, 943; 600/411, 600/300
See application file for complete search history.

(56) References Cited

U.S. PATENT DOCUMENTS

| | | | |
|---|---|---|---|
| 4,939,464 A | 7/1990 | Hammer | |
| 5,197,474 A | 3/1993 | Englund et al. | |
| 5,525,905 A | 6/1996 | Mohapatra et al. | |
| 5,615,430 A | 4/1997 | Nambu et al. | |
| 6,263,043 B1 | 7/2001 | Maschke | |
| 6,302,579 B1 | 10/2001 | Meyer et al. | |
| 6,590,391 B1 | 7/2003 | Shudo et al. | |
| 6,603,991 B1 | 8/2003 | Karmalawy et al. | |
| 6,946,841 B2 | 9/2005 | Rubashov | |
| 6,961,606 B2 | 11/2005 | DeSilets et al. | |
| 7,120,223 B2 * | 10/2006 | Nafstadius | 378/20 |

(Continued)

FOREIGN PATENT DOCUMENTS

| | | |
|---|---|---|
| JP | 08206104 A | 8/1996 |
| JP | 2001314420 A | 11/2001 |
| WO | 03003038 A1 | 1/2003 |
| WO | 2006119085 A2 | 11/2006 |

OTHER PUBLICATIONS http://www.imris.com/products MR 15 and OR Table, accessed Aug. 21, 2008.

*Primary Examiner* — Fredrick Conley

(57) ABSTRACT

A hybrid imaging system and a patient bed for same are disclosed. The hybrid imaging system includes a magnetic resonance scanner and a second modality imaging system spaced apart from the magnetic resonance scanner by a gap. In some embodiments, the gap is less than seven meters. The patient bed is disposed at least partially in the gap between the magnetic resonance scanner and the second modality imaging system, and includes a linearly translatable patient support pallet aligned to be selectively moved into an examination region of the magnetic resonance scanner for magnetic resonance imaging and into an examination region of the second modality imaging system for second modality imaging. In some embodiments, a linear translation range of the linearly translatable pallet is less than five times a length of the patient support pallet along the direction of linear translation.

15 Claims, 7 Drawing Sheets

(56) References Cited

U.S. PATENT DOCUMENTS

| | | | |
|---|---|---|---|
| 2001/0003218 A1* | 6/2001 | Schaefer | 5/601 |
| 2003/0004405 A1 | 1/2003 | Townsend et al. | |
| 2003/0078489 A1* | 4/2003 | DeSilets et al. | 600/407 |
| 2005/0060804 A1 | 3/2005 | Heinl et al. | |
| 2005/0113667 A1 | 5/2005 | Schlyer et al. | |
| 2005/0152492 A1 | 7/2005 | Yakubovsky et al. | |
| 2006/0052685 A1 | 3/2006 | Cho et al. | |
| 2006/0251312 A1 | 11/2006 | Krieg | |

* cited by examiner

PATIENT BED FOR PET/MR IMAGING SYSTEMS

CROSS REFERENCE TO RELATED APPLICATIONS

This application is a continuation of PCT application number PCT/US2007/081458 filed Oct. 16, 2007 which claims the benefit of U.S. provisional application Ser. No. 60/863,637 filed Oct. 31, 2006, which is incorporated herein by reference.

BACKGROUND OF THE INVENTION

The present application relates to the medical imaging arts. It particularly relates to combined magnetic resonance (MR) and positron emission tomography (PET) imaging systems, and is described with particular reference thereto. The following relates more generally to imaging systems that combine the MR imaging modality with a modality employing energized particles, such as the aforementioned PET modality, single photon emission computed tomography (SPECT) modality, transmission computed tomography (CT) modality, a radiation therapy modality, or so forth.

In a hybrid imaging system, two or more medical imaging modalities are integrated into the same facility or room, or even into the same gantry. Hybrid imaging systems enable medical personnel to combine the advantages of the constituent modalities to acquire more useful information about the patient. Hybrid imaging systems also make it easier to spatially and temporally register images from the constituent modalities as compared with acquiring such images by discrete, separate imaging systems. Separate imaging systems have a longer lag time between studies, and make it difficult to minimally disturb the patient between studies.

The advantages of hybrid imaging systems have been realized commercially. For example, the Precedence SPECT/CT system available from Philips Medical Systems, Eindhoven, The Netherlands provides a CT scanner and a gamma camera for SPECT imaging. The latter includes two radiation detector heads mounted on robotic arms offset from the CT gantry along the patient end of the system. An extended patient couch is used to allow for adequate axial movement of the patient. Thus, both CT and SPECT imaging capability are available with limited modifications to either the CT gantry or the spatially separated gamma camera. Similarly, the Gemini PET/CT system also available from Philips Medical Systems, Eindhoven, The Netherlands provides both PET and CT imaging modalities.

However, construction of a hybrid imaging system including a magnetic resonance (MR) scanner and a second modality imaging system employing high energy particles or photons (such as SPECT or PET) is challenging. In a typical magnetic resonance imaging facility, a magnetic resonance scanner is located in a specially designed radio frequency isolation space created by a surrounding Faraday cage-type radio frequency shield. The radio frequency isolation space protects the sensitive magnetic resonance detection system from extraneous radio frequency interference. Additionally, the radio frequency (RF) shield helps reduce radiofrequency emissions from the MR scanner's RF transmit coils to the environment external to the scanner room. Problematically, the electronics for radiation detectors used in PET scanners or other imaging systems that detect high energy particles or photons typically generate high levels of radio frequency interference. Conversely, the magnetic field that is produced by the magnetic resonance scanner distorts the response of the photon detectors used in the PET scanner. Consequently, when considering placement in the same room with close proximity, there is an inherent practical incompatibility between a magnetic resonance scanner and an imaging system that detects high energy particles or photons.

Cho et al, U.S. Published Application No. 2006/0052685, proposes overcoming this inherent incompatibility by disposing the PET scanner outside of the radio frequency isolation space containing the magnetic resonance scanner. Unfortunately, this approach vitiates many of the benefits of a hybrid MR/PET system. The patient must be transferred between the MR and PET systems through a shutter-type opening in a wall of the radio frequency isolation room containing the MR scanner. Medical personnel must move back and forth between the room containing the PET scanner and the radio frequency isolation room containing the MR scanner. The system of Cho et al. includes a long railway system for transferring the patient between the MR and PET scanners located in separate rooms. The patient may find such a long-distance transfer uncomfortable, and shifting or other movement of the patient during such a long transfer can introduce spatial registration errors in images acquired by the MR and PET. Moreover, difficulties can arise in transferring local coils used in magnetic resonance imaging across the long rail distance.

Another approach that has been proposed is to integrate the PET radiation detectors into the gantry of the magnetic resonance scanner. It has been suggested that by judicious positioning of the radiation detectors at null points of the magnetic field, the effect of stray magnetic fields on the PET radiation detectors can be reduced. However, this approach does not address the issue of radio frequency interference from the radiation detectors interfering with the magnetic resonance detection system. Additionally, the integrated PET radiation detectors occupy valuable bore space in the MR scanner.

A variation on the integrated approach, disclosed in Hammer, U.S. Pat. No. 4,939,464, is to integrate only the scintillators of the PET scanner into the magnetic resonance scanner. Scintillation light produced by radiation detection events is captured and transferred by fiber optics to remote optical detectors of the PET system. This approach reduces, but does not eliminate, MR bore space usage by PET components, and additionally introduces sensitivity issues in the PET system due to optical losses in the extensive fiber optical light coupling systems. Moreover, while arranging the light detection electronics remotely is beneficial, some types of scintillation crystals exhibit spontaneous radioactivity that can still produce substantial radio frequency interference.

A disadvantage of existing hybrid approaches is that these approaches are not conducive to retrofitting an existing magnetic resonance scanner. The approach of Cho et al. requires availability of a PET scanner room suitably located adjacent to the radio frequency isolation room of the magnetic resonance scanner, and further requires cutting a passthrough into the separating wall and adding a complex and bulky railway system for coupling the PET and MR scanners located in separate rooms. Approaches that integrate the PET radiation detectors into the MR scanner bore similarly add complexity to the retrofitting process, and may be unworkable with some existing MR scanners.

SUMMARY OF THE INVENTION

In accordance with one aspect, a patient bed is disclosed, including: a base disposed between a magnetic resonance scanner and a second modality imaging system, the second modality being other than magnetic resonance; and a linearly translatable patient support pallet supported by the base and aligned to be selectively moved into an examination region of the magnetic resonance scanner for magnetic resonance imaging and into an examination region of the second modality imaging system for second modality imaging, a linear translation range of the linearly translatable pallet being less than five times a length of the patient support pallet along the direction of linear translation.

In accordance with another aspect, a hybrid imaging system is disclosed, including: a magnetic resonance scanner; a second modality imaging system spaced apart from the magnetic resonance scanner by a gap of less than seven meters, the second modality being other than magnetic resonance; and a patient bed disposed at least partially in the gap between the magnetic resonance scanner and the second modality imaging system, the patient bed including a linearly translatable patient support pallet aligned to be linearly translated into an examination region of the magnetic resonance scanner for magnetic resonance imaging and into an examination region of the second modality imaging system for second modality imaging.

In accordance with another aspect, a retrofit method is disclosed, including: disposing a second modality imaging system within a radio frequency isolated room containing a magnetic resonance scanner with the second modality imaging system spaced apart from the magnetic resonance scanner by a gap of less than seven meters and with the examination regions of the respective magnetic resonance scanner and second modality imaging systems linearly aligned, the second modality being other than magnetic resonance; and disposing a patient bed at least partially in the gap between the magnetic resonance scanner and the second modality imaging system with a linearly translatable patient support pallet of the patient bed aligned to be linearly translated into the examination region of the magnetic resonance scanner for magnetic resonance imaging and into the examination region of the second modality imaging system for second modality imaging.

In accordance with another aspect, a patient bed is disclosed, including: a base disposed between a magnetic resonance scanner and a second modality imaging system, the second modality being other than magnetic resonance; a translatable patient support pallet supported by the base and aligned to be selectively moved into an examination region of the magnetic resonance scanner for magnetic resonance imaging and into an examination region of the second modality imaging system for second modality imaging; a radio frequency device or device port disposed with the pallet; and a radio frequency cable having a first end coupled with the radio frequency device or device port.

In accordance with another aspect, a hybrid imaging system is disclosed, including: a magnetic resonance scanner disposed in a radio frequency isolation room; a second modality imaging system disposed in the radio frequency isolation room with the magnetic resonance scanner, the second modality being other than magnetic resonance; and a patient bed disposed in the radio frequency isolation room at least partially in a gap between the magnetic resonance scanner and the second modality imaging system, the patient bed including a patient support pallet for transferring a patient into an examination region of the magnetic resonance scanner for magnetic resonance imaging and into an examination region of the second modality imaging system for second modality imaging.

In accordance with another aspect, a patient bed is disclosed, including: a base disposed between a magnetic resonance scanner and a second modality imaging system, the second modality being other than magnetic resonance; and a patient support pallet supported by the base and movable in a first direction into an examination region of the magnetic resonance scanner for magnetic resonance imaging and movable in a second direction opposite the first direction into an examination region of the second modality imaging system for second modality imaging.

One advantage resides in providing a spatially compact hybrid imaging system.

Another advantage resides in providing spatial compactness without compromising ease of patient loading through the availability of height adjustment and access to the patient bed from an end of the bed.

Another advantage resides in advantageously placing the patient bed in space between a magnetic resonance scanner and a second modality imaging system that is provided to isolate the two imaging systems from one another.

Another advantage resides in providing convenient radio frequency cabling in a hybrid imaging system that includes a magnetic resonance scanner.

Another advantage resides in enabling magnetic resonance scanning followed by PET or other second modality imaging, or vice versa, without disturbing the subject except for short-range translational motion.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 1 diagrammatically depicts the hybrid imaging system during patient loading;

FIG. 2 diagrammatically depicts the hybrid imaging system with the patient table elevated into alignment with the constituent imaging systems, but with the second modality imaging system in its less proximate position;

FIG. 3 diagrammatically depicts the hybrid imaging system with the second modality imaging system moved into its more proximate position, with a portion of the patient bed overlapped by the examination region of the hybrid imaging system shown in phantom;

FIG. 4 diagrammatically depicts the hybrid imaging system with the patient table translated into the magnetic resonance scanner for brain imaging, with selected internal components of the magnetic resonance scanner shown in phantom; and FIG. 5 diagrammatically depicts the hybrid imaging system with the patient table translated into the second modality imaging system for brain imaging, with selected internal components of the second modality imaging system shown in phantom.

DETAILED DESCRIPTION OF THE INVENTION

Figure 1:
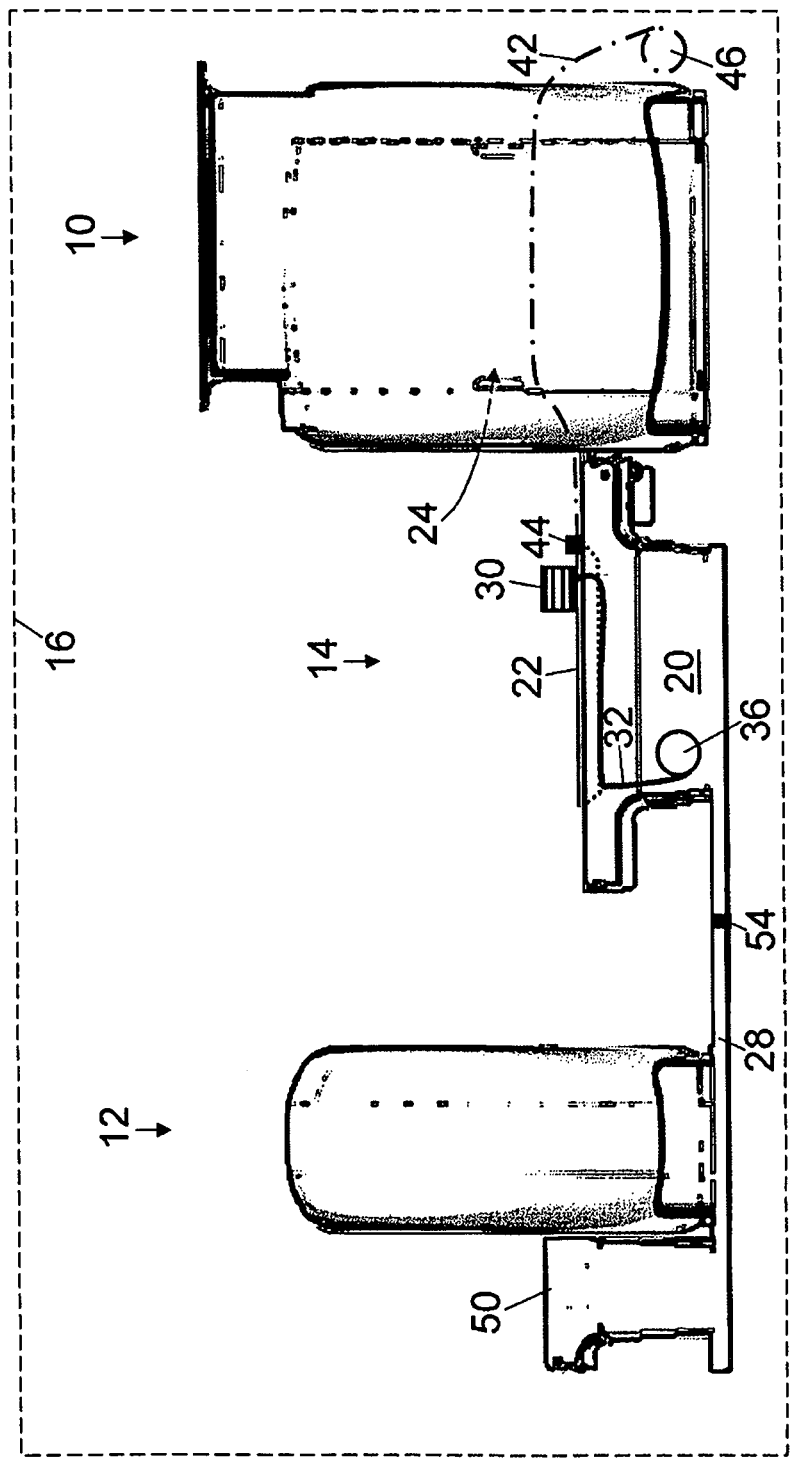
FIGS. 1-5 diagrammatically depict a hybrid imaging system at various stages of an example brain imaging session, including diagrammatic depiction of two alternative radio frequency cabling arrangements for connecting a local head coil used in the magnetic resonance imaging portion of the brain imaging session.

With reference to FIGS. 1-5, a hybrid imaging system includes a magnetic resonance scanner 10, a second modality imaging system 12, and a patient support, such as an illustrated patient bed 14, disposed between the magnetic resonance scanner 10, a second modality imaging system 12. A radio frequency shield substantially surrounds and defines a radio frequency isolated room or space 16. The magnetic resonance scanner 10, the second modality imaging system 12, and patient bed 14 are disposed within the radio frequency isolated room. The magnetic resonance scanner 10 in some embodiments is a commercial magnetic resonance scanner such as an Achieva or Intera magnetic resonance scanner available from Philips Medical Systems, Eindhoven, The Netherlands. More generally, the magnetic resonance scanner 10 can be substantially any type of scanner, such as the depicted horizontal cylindrical bore magnet scanner, an open bore scanner, or so forth.

The radio frequency isolated room 16 is constructed to substantially isolate the sensitive magnetic resonance receive system of the magnetic resonance scanner 10 from outside radio frequency interference. The radio frequency shield defining the radio frequency isolated room 16 can employ substantially any known shielding arrangement, and typically comprises a room-sized Faraday cage surrounding the walls, ceiling, and the floor, of a physical room. The radio frequency isolated room 16 is of a typical size for a magnetic resonance imaging facility, such as for example a room having a floor area of about 7×9 meters, although larger or smaller rooms and/or rooms of different floor area dimensions are also contemplated. As is known in the magnetic resonance arts, radio frequency-tight access doors and windows are advantageously provided in the radio frequency isolated room.

The second modality imaging system 12 is in some embodiments a positron emission tomography (PET) scanner. However, other second modality imaging systems can be used, such as a gamma camera for performing SPECT imaging, a transmission computed tomography (CT) scanner, or so forth. Typically, the second modality imaging system 12 is configured to detect at least one of high energy particles and high energy photons. For example, a PET scanner detects 511 keV photons generated by positron-electron annihilation events; a gamma camera is configured to detect selected particles, gamma rays, or so forth emitted by a selected radiopharmaceutical; a CT scanner detects transmitted x-rays; and so forth. In some embodiments the second modality imaging system 12 is an Allegro PET scanner available from Philips Medical Systems, Eindhoven, The Netherlands. It is also contemplated for the second modality imaging system 12 to itself comprise two or more constituent imaging systems. For example, the second modality imaging system 12 may be a Precedence SPECT/CT system or a Gemini PET/CT system, both also available from Philips Medical Systems, Eindhoven, The Netherlands.

The arrangement of the patient bed 14 between the magnetic resonance scanner 10 and the second modality imaging system 12 is advantageous because it physically separates the two different constituent imaging systems 10, 12. This physical separation reduces the adverse effect of the static magnetic field generated by the magnetic resonance scanner 10 on the second modality imaging system 12, and also reduces the adverse effect of the ferromagnetic mass and radio frequency interference sourcing of the second modality imaging system 12 on the magnetic resonance scanner 10. The patient bed 14 includes a base 20 and a linearly translatable patient support pallet 22 coupled with the base 20 and aligned to be selectively moved into an examination region 24 of the magnetic resonance scanner 10 for magnetic resonance imaging and into an examination region 26 of the second modality imaging system 12 for second modality imaging (e.g., PET imaging). The linearly translatable patient support pallet 22 is moved automatically by a motor (not shown) mounted in the base 20 or in one of the imaging systems 10, 12. Alternatively, the motor may be omitted, and the pallet 22 translated manually. Optionally, the patient support pallet 22 includes at least one handhold or other tactile feature (not shown) configured to facilitate manual translation of the patient support pallet.

FIG. 1 diagrammatically depicts the arrangement of the hybrid system during patient loading. (Note, the associated patient who is loaded and imaged is not shown in the drawings). The base 20 is optionally configured to be lowered during patient loading to enable easier loading of the patient onto the patient support pallet 22. The second modality imaging system 12 is optionally mounted on rails 28 to enable the second modality imaging system 12 to be translated into a less proximate position shown in FIGS. 1 and 2, or into a more proximate position shown in FIGS. 3-5. The second modality imaging system 12 is relatively more proximate to the magnetic resonance scanner in the more proximate position, and is relatively less proximate to (or in other words, relatively more remote from) the magnetic resonance scanner 10 in the less proximate position. In the less proximate (i.e., more remote) position, a gap is optionally present between the end of the patient bed 14 and the second modality imaging system 12. In some embodiments, the optional gap is large enough to enable medical personnel to walk between the patient bed 14 and the second modality imaging system 12 to facilitate patient access. It is also contemplated to keep the second modality imaging system stationary, and to mount the magnetic resonance scanner on rails to enable relative movement of the two constituent imaging systems.

The illustrated imaging session is a brain imaging session employing a local head coil 30, which may be a receive-only coil, a transmit-only coil, or a transmit/receive coil. More generally, imaging of substantially any anatomical portion of the patient, or a whole-body imaging session, may be performed. In the illustrative brain imaging session, the local coil 30 is used for magnetic resonance receiving, and optionally is also used for transmitting magnetic resonance exciting radio frequency pulses. For other imaging sessions, other local coils or coil arrays may be used, such as a local arm coil, a local multi-channel or SENSE coil array configured to image the torso, or so forth. Some imaging sessions may be performed without any local coil, instead using a whole body coil or other coil (not shown) mounted in the magnetic resonance scanner 10. The imaging session may also involve administration of a suitable magnetic contrast agent for enhanced magnetic resonance contrast, and/or of a radiopharmaceutical to provide radioactivity for imaging by the second modality imaging system 12, or so forth. In some approaches, fiducial markers configured to be imaged by both the magnetic resonance scanner 10 and the second modality imaging system 12 may be placed onto the patient to improve or enable post-acquisition spatial registration of images acquired by the two modalities.

The local head coil 26 is coupled with the remainder of the magnetic resonance receive system of the magnetic resonance scanner 10 by a radio frequency cable, such as a coaxial cable. In FIGS. 1-5, two cabling systems are shown as examples. In a first cabling system, a radio frequency cable 32 (shown using a solid line) remains connected with the local head coil 30 throughout both the magnetic resonance imaging and the second modality imaging. The radio frequency cable 32 is configured to pass underneath the linearly translatable patient support pallet 22 and to have a first end remain coupled with the local head coil 30 (as shown) or with a device port connecting with the head coil 30, both when the patient support pallet 22 is moved into the examination region 24 of the magnetic resonance scanner 10 and also when the patient support pallet 22 is moved into the examination region 26 of the second modality imaging system 12. A tensioner, spool 36 or other take-up mechanism is optionally disposed in or near the base 20 to take up the cable slack.

In a second, alternative cabling system, a radio frequency cable 42 (shown using a dot-dashed line) is configured with an automatic disconnect 44 that disconnects the first end of the radio frequency cable from the head coil 30, or from a device port connecting with the head coil 30 (as shown) responsive to the patient support pallet 22 being moved into or toward the examination region 26 of the second modality imaging system 12. A tensioner, spool 46 or other take-up mechanism is optionally disposed near the magnetic resonance scanner 10 on the end of the bore 60 of the magnetic resonance scanner 10 away from the patient support 14 to take up the cable slack.

Figure 2:
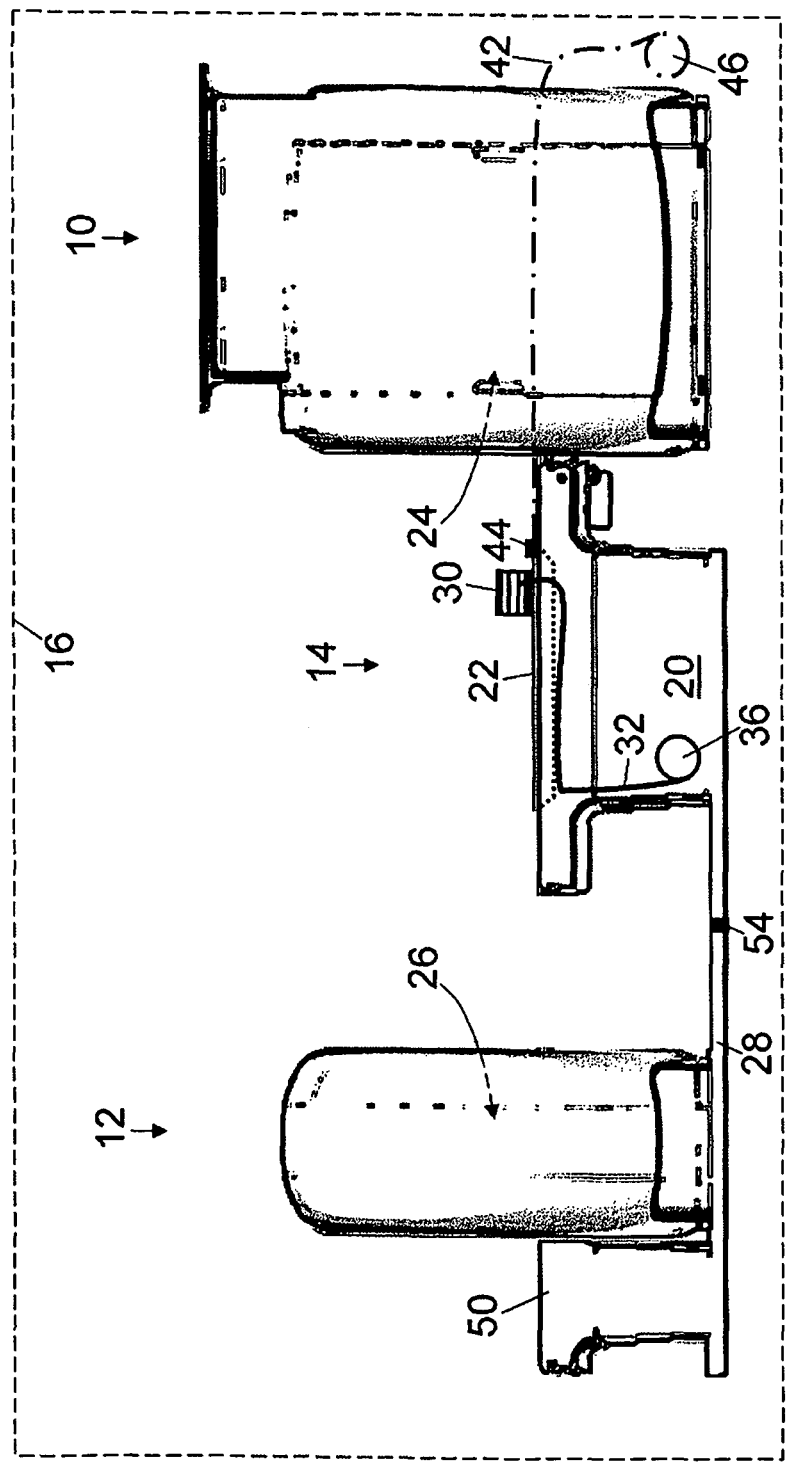

FIG. 2 diagrammatically shows the hybrid system after patient loading and after the base 20 of the patient bed 14 has been adjusted in height to raise the patient support pallet 22 into alignment with the examination regions 24, 26 of the imaging systems 10, 12.

Figure 3:
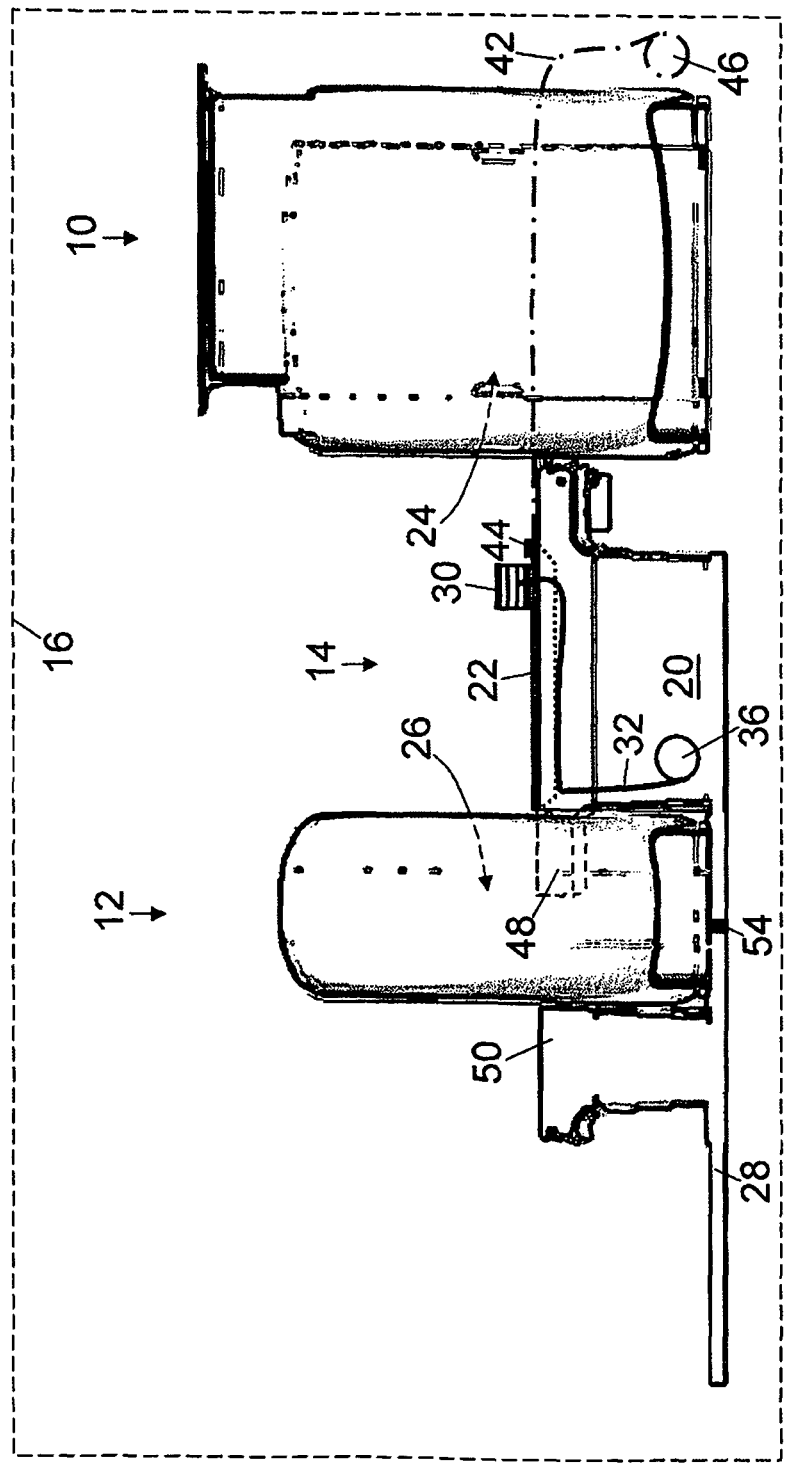

FIG. 3 diagrammatically shows the hybrid system after the additional operation of moving the second modality imaging system 14 into the more proximate position. In this more proximate position, the linearly translatable patient support pallet 22 coupled with the base 20 can be translated into either examination region 24, 26 for imaging. As indicated by phantom in FIG. 3, in the illustrated embodiment a portion 48 of the patient bed 14 overlaps the examination region 26 of the second modality imaging system 12 when the second modality imaging system 12 is in the more proximate position. This arrangement is convenient to enable mechanical coupling of a patient support extension 50 or other support of the second modality imaging system 12 with the patient bed 14. In other embodiments, no such overlap is provided, and the coupling occurs at the edge of the examination region 26 or outside of the examination region 26. In some embodiments, it is contemplated for the second modality imaging system to include no patient beam or other support, and for the patient bed to instead extend in cantilevered fashion through the examination region of the second modality imaging system.

Figure 4:
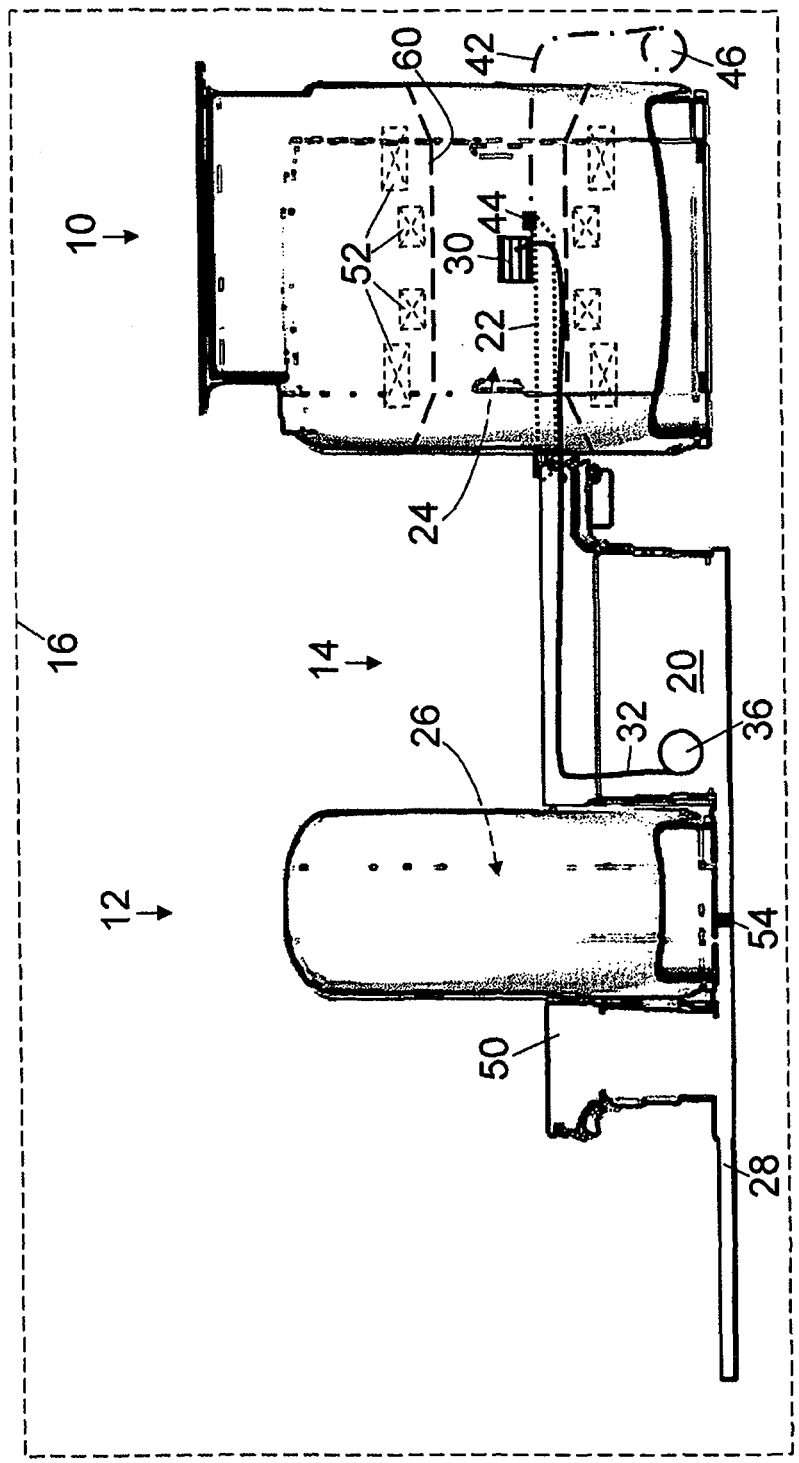

FIG. 4 diagrammatically shows the hybrid system after the patient support pallet 22 has been moved into the examination region 24 of the magnetic resonance scanner 10 for commencement of magnetic resonance imaging. In FIG. 4, the second modality imaging system 12 is not in use, but is in its more proximate position along the rails 28. Additionally or alternatively, magnetic resonance imaging may be performed with the second modality imaging system 12 not in use and in its less proximate position along the rails 28 (for example, in the position along the rails shown in FIGS. 1 and 2). The position of the second modality imaging system 12 typically affects the static magnetic field homogeneity of the magnetic resonance scanner 10, because the second modality imaging system typically includes a large mass of metal or other ferromagnetic material that can distort the static magnetic field. Optionally, shim coils 52 are provided in the magnetic resonance scanner 10 that produce a compensatory magnetic field to correct for static magnetic field distortion produced by the presence of the second modality imaging system 12. Moreover, it will be recognized that this distortion depends upon whether the second modality imaging system 12 is in the less proximate position (FIGS. 1 and 2) or in the more proximate position (FIGS. 3-5) since the distance between the second modality imaging system 12 and the magnetic resonance scanner 10 is different for these two positions. In some embodiments, the shim coils 52 are configured as switchable magnetic shims configured to have a first switched setting shimming the static magnetic field of the magnetic resonance scanner 10 with the second modality imaging system 12 in the more proximate position (FIGS. 3-5) and having a second switched setting shimming the static magnetic field with the second modality imaging system 12 in the less proximate (i.e., more remote) position (FIGS. 1 and 2). For example, an inductive, weight-based, or otherwise operative sensor 54 can be included in or with the rails 28 to detect when the second modality imaging system 12 is in the more proximate position, and the output of the sensor 54 used to switch the shim coils 52 between the two shim settings. In other embodiments, manual shim switching, optically triggered shim switching, or other control mechanisms can be used in place of the rail-based sensor 54. In one approach, the shim coils 52 may include first (via the MR gradient coils) and second order shim coils. In another approach, shim coils 52 specifically configured to shim for the two states of operation may be used.

With continuing reference to FIG. 4, for magnetic resonance imaging the patient support pallet 22 is linearly translated into a bore 60 (edges indicated by dashed lines in FIG. 4) of the magnetic resonance scanner 10. In the illustrated example, the bore 60 has flared ends such as are sometimes used to give the bore a more "open" feel, or to tailor the shape of the magnetic field, or so forth. The patient is typically positioned for magnetic resonance imaging with the anatomical region of interest (denoted by the position of the head coil 30 in the instant brain imaging example) centered in the examination region 24 of the magnetic resonance scanner 10. Note that as the patient support pallet 22 moves into the magnetic resonance scanner 10, additional length of the radio frequency cable 32 is drawn off the spool 36. In the alternative radio frequency cabling arrangement, as the patient support pallet 22 moves into the magnetic resonance scanner 10 a length of the radio frequency cable 42 is taken back onto the spool 46 to take up the cable slack.

Once the magnetic resonance imaging is completed, the patient support pallet 22 bearing the patient is withdrawn from the examination region 24 of the magnetic resonance scanner 10.

Figure 5:
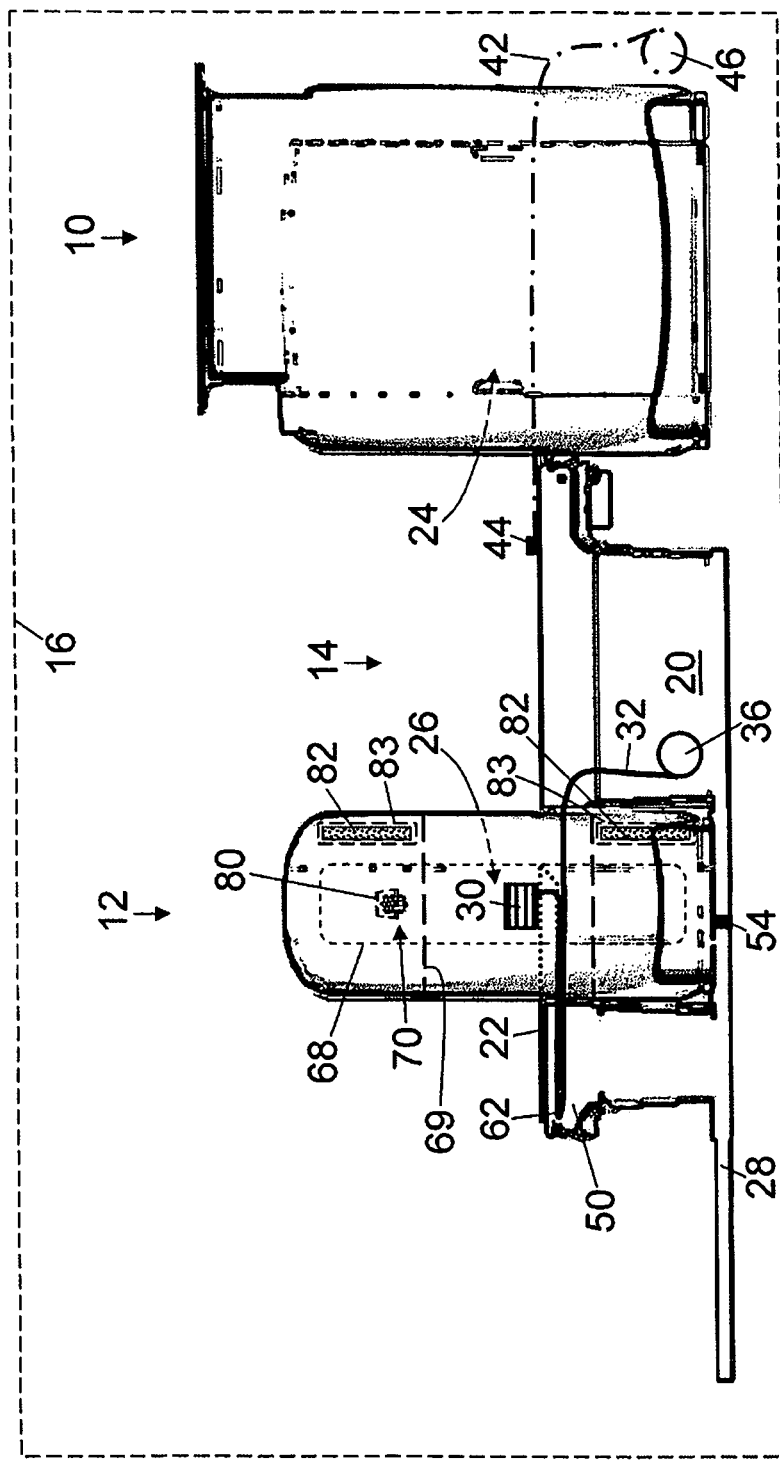

With reference to FIG. 5, if it is desired to perform second modality imaging, the patient support pallet 22 is moved into the examination region 26 of the second modality imaging system 12. Note that this entails some flexibility on the part of the radio frequency cabling system. When using the cable 32, the movement into the second modality imaging system is accommodated as follows. The cable 32 is pinned at a pinning point 62 (labeled only in FIG. 5) to an end of the patient support pallet 22. As the patient support pallet 22 is withdrawn from the examination region 24 of the magnetic resonance scanner 10 (assuming that magnetic resonance imaging was done first), the spool 36 takes up the cable slack. Once the pinning point 62 moves past the spool 36 and toward the second modality imaging system 12, the spool begins to put out additional length of cable to accommodate the pallet movement. The spool 36 includes sufficient cable length to accommodate the "doubling up" of the cable along the length of the pallet when the pallet 22 is fully inserted into the examination region 26 of the second modality imaging system 12. Note that when using this arrangement, the order of imaging is reversible—that is, the second modality imaging could be performed first, followed by the magnetic resonance imaging.

With continuing reference to FIG. 5, if on the other hand the alternative cabling arrangement is used, then the magnetic resonance imaging should be performed first. Then, as the patient support pallet 22 is moved out of the bore of the magnetic resonance scanner 10, the spool 46 plays out additional length of cable 42 to accommodate the pallet movement. However, as the patient support pallet 22 continues to move (or be moved) toward the second modality imaging system 12, the cable 42 extends to its full length. At this point, further movement of the patient support pallet 22 toward the second modality imaging system 12 causes the automatic disconnect 44 to disconnect the end of the cable 42 from the head coil 30, or from the port to which the head coil is attached. The patient support pallet 22, and the head coil 30, continue to move (or be moved) into the examination region 26 of the second modality imaging system 12 for commencement of second modality imaging. To allow second modality imaging to be performed first, the automatic disconnect 44 can be configured as a dockable connection that allows for automatic connect as well as disconnect.

Figure 6:
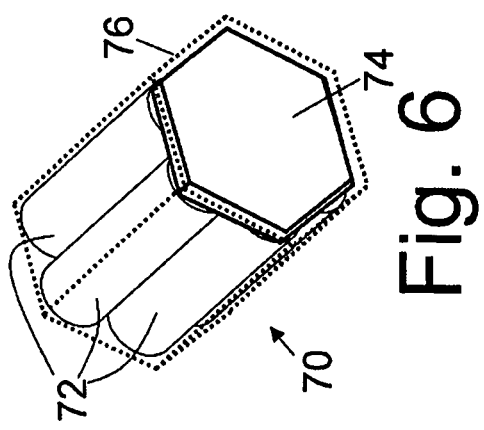
FIG. 6 diagrammatically depicts a hexagonal arrangement of seven photomultiplier tubes substantially enclosed surrounded by an enclosure constructed of ferromagnetic material.

With continuing reference to FIG. 5 and with further reference to FIG. 6, the second modality imaging system 12 includes a ring of radiation detectors 68 surrounding a bore 69 of the second modality imaging system 12. In FIG. 5 one radiation detector module 70 of the ring of radiation detectors 68 is shown for illustrative purposes. FIG. 6 depicts a perspective view of the radiation detector module 70 viewed from a point inside the examination region 26. The radiation detector module 70 includes seven photomultiplier tubes 72 arranged hexagonally and viewing a hexagonal scintillator 74. The static magnetic field produced by the magnetic resonance scanner 10 has the potential to adversely affect operation of the photomultiplier tubes 72. In some embodiments, this effect is reduced by providing magnetic shielding for the radiation detectors, for example by substantially surrounding the photomultiplier tubes 72 with an enclosure 76 of a ferromagnetic material. The enclosure 76 can be a ferromagnetic housing or shell substantially enclosing the photomultiplier tubes 72, or a ferromagnetic thin film coating the photomultiplier tubes 72, or so forth. Additionally, the enclosure 76 can reduce radio frequency interference from the photomultiplier tubes that might otherwise adversely affect the sensitive magnetic resonance detection system of the magnetic resonance scanner 10. To enhance the radio frequency shielding of the enclosure a layer of copper or other non-ferrous but highly electrically conducting material may be used in combination with the ferromagnetic material. The enclosure 76 is advantageously hexagonal in shape to enable close packing of the modules 70 in the ring of radiation detectors 68; however, other geometries can be used. If the enclosure 76 additionally substantially surrounds the scintillator crystal 74, then radio frequency interference that may be produced by random radioactive decay events in the scintillator are also substantially shielded away from the magnetic resonance scanner 10. At least that portion of the enclosure 76 in front of the radiation-detecting surface of the scintillator crystal 74 should be made thin enough that the radiation being detected (e.g., 511 keV photons in the case of a PET scanner) can pass through substantially unimpeded.

Figure 7:
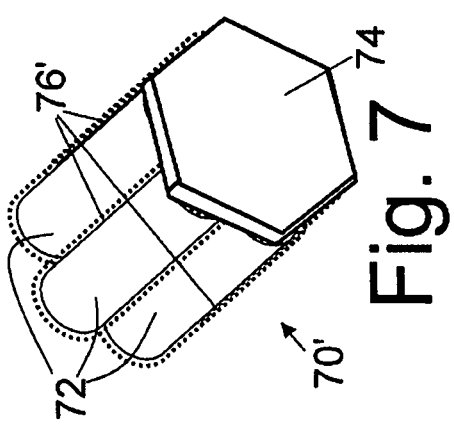
FIG. 7 diagrammatically depicts an alternative arrangement of a single photomultiplier tube substantially surrounded by an enclosure constructed of ferromagnetic material.

With reference to FIG. 7, in another approach for providing magnetic shielding of the radiation detectors, a modified module 70' includes the photomultiplier tubes 72 individually shielded by individual enclosures 76' comprised of ferromagnetic material. The enclosure 76' can be a ferromagnetic outer tube or tubular housing or shell substantially enclosing each photomultiplier tubes 72, or a ferromagnetic thin film coating each photomultiplier tubes 72, or so forth. In the embodiment illustrated in FIG. 7, the scintillator crystal 74 is left unshielded.

Figure 8:
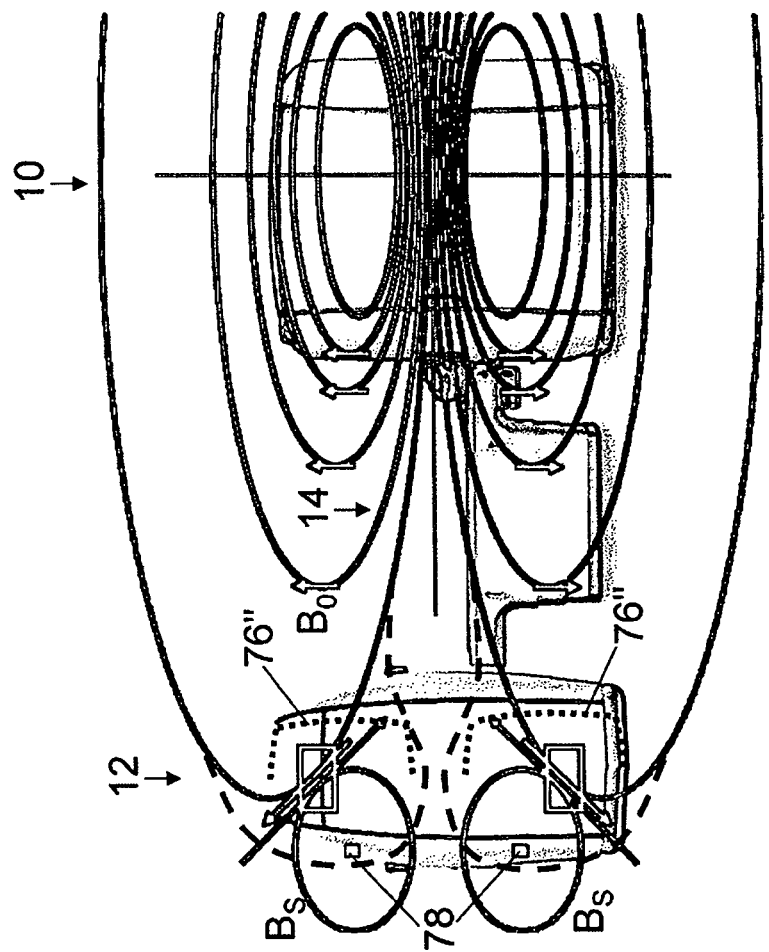
FIG. 8 diagrammatically depicts active and partial passive shielding arrangements for the radiation detectors of the second modality imaging system.

With reference to FIG. 8, active magnetic shielding is also contemplated. As shown in FIG. 8, the static magnetic field $B_0$ produced by the magnetic resonance scanner 10 can be at least partially canceled by a shielding magnetic field Bs produced by shield coils 78 (diagrammatically indicated in FIG. 8 by center points for generation of the shielding magnetic field $B_S$) suitably positioned on the second modality imaging system 12. Because the stray static magnetic field $B_0$ at the photomultiplier tubes is small (typically about 15 gauss in some hybrid systems), the shield coils 78 can be relatively low power devices.

With continuing reference to FIG. 8, as yet another alternative, passive magnetic shielding 76" (shown in FIG. 8 by dotted lines) that is not substantially encompassing can be arranged to redirect the stray magnetic field $B_0$ from the magnetic resonance scanner 10 at the radiation detectors 68 to a direction less interfering with the radiation detectors 68. FIG. 8 shows the magnetic flux lines redirected by the passive magnetic shielding 76" as dashed lines. The passive magnetic shielding 76, 76', 76" can be any ferromagnetic material such as iron, steel, or so forth, or a mu-metal material.

In the illustrated embodiments, the radiation detectors employ photomultiplier tubes, which have a relatively high sensitivity to stray magnetic fields. Typically, one or more of the magnetic shielding mechanisms 76, 76', 76", 78 is provided to reduce stray magnetic fields from the magnetic resonance scanner 10 at the radiation detectors 68, 70, 70' of the second modality imaging system 12 to less than a few Gauss, the required reduction depending on field orientation in relation to the detectors, in particular the photomultiplier tubes. However, the shielding can alternatively deflect the magnetic flux lines to flow parallel to an axis of the anode and cathode of each photomultiplier tube, which substantially reduces the effect of the magnetic field on operation of the photomultiplier tube. In this case, higher fringe magnetic fields can be tolerated. In other embodiments, solid state detectors may be used which have much lower sensitivity to stray magnetic fields. In these embodiments, the passive and/or active magnetic shielding is can be omitted.

With reference back to FIG. 5, the radiation detectors have associated electronics, such as local printed circuit board electronics 80 disposed with the radiation detector modules, one or more centralized electronics units 82 disposed in the gantry (as shown) or remotely, and so forth. The magnetic resonance scanner 10 is sensitive to one or more magnetic resonance frequencies. The primary magnetic resonance frequency is usually that of proton imaging. Other magnetic resonance frequencies of concern may include spectroscopic frequencies implicated in magnetic resonance spectroscopy, sub-frequencies used in sampling and demodulation of the magnetic resonance data, and so forth. The magnetic resonance frequencies of concern may include, for example, those associated with $^1$H, $^{13}$C, $^{19}$F, $^{23}$Na, $^{31}$P, and other nuclei that exhibit magnetic resonance properties. Heretofore, concern about radio frequency interference produced by the electronics 80, 82 of the second modality imaging system 12 has been a substantial bar to inclusion of such second modality imaging system 12 in the same radio frequency isolation room 16 as the magnetic resonance scanner 10. However, radio frequency interference can be reduced or eliminated while still keeping the electronics 80, 82 in the radio frequency isolation room 16 with the magnetic resonance scanner 10. This can be done by recognizing that most radio frequency interference comes from switching aspects of the electronics. Principle sources of switching include (i) switching power supplies, such as are used to operate the radiation detectors 68; and (ii) dynamic memory and synchronous digital processing electronics which are clocked at a high frequency.

The electronics 80, 82 disposed in the radio frequency isolation room 16 with the magnetic resonance scanner 10 optionally do not include switching power supplies. For example, linear power supplies can be used, which do not switch at high frequency and hence do not produce substantial radio frequency interference. Alternately, the switching power supplies can be located externally to the RF shielded room 16 and the power supplied through electrically filtered penetrations of the room 16.

Similarly, the electronics 80, 82 disposed in the radio frequency isolation room 16 with the magnetic resonance scanner 10 optionally do not include dynamic memory, synchronously clocked digital electronics, or both. For a typical PET, SPECT, or CT system, the number of detectors is large, numbering in the thousands or tens of thousands, and each detector outputs a stream of data that must be stored. Accordingly, a typical PET, SPECT, or CT system includes well over a gigabyte of dynamic memory. In the electronics 80, 82, this memory is advantageously optionally replaced by unclocked static memory, such as flash memory or the like, which is not clocked at high frequency and hence does not produce substantial radio frequency interference. In similar fashion, clocked synchronous digital electronic processing circuitry is optionally replaced by asynchronous digital electronic processing circuitry, or even by analog processing circuitry. Alternatively, the electronics 80, 82 can be put into a quiet mode where the clocks for dynamic memory and other electronics can be turned off and power supplies for radiation detectors 68 disabled either manually or under system control during magnetic resonance imaging.

Additionally or alternatively, the electronics 80, 82 include other features that reduce radio frequency interference with the magnetic resonance scanner 10. Recognizing that the principal concern is with the highly sensitive magnetic resonance detection system of the magnetic resonance scanner 10, the electronics 80, 82 optionally are configured such that the produced radio frequency interference is spectrally separated from the magnetic resonance frequency. A suitable approach is to use electronics 80, 82 with clocking frequencies and/or switching frequencies for switching power supplies that are not at the magnetic resonance frequency or frequencies, and that do not have harmonics at the magnetic resonance frequency or frequencies. Additionally, the electronics 80, 82 optionally include one or more notch filters tuned to block inadvertent generation of radio frequency interference at the magnetic resonance frequency or frequencies of the magnetic resonance scanner 10, such as might arise from random thermal noise or so forth even in electronics that are tuned away from the magnetic resonance frequency. Still further, the centralized electronics 82 can include radio frequency shielding 83 substantially surrounding the centralized electronics. Alternatively, the electronics can be located outside the radio frequency isolation room 16.

Using one or more of these approaches (such as omitting clocked memory, omitting switching power supplies, using electronics operating at frequencies selected to avoid producing radio frequency interference at the magnetic resonance frequency or frequencies, employing suitable notch filters, and so forth) the electronics 80, 82 can be included in the same radio frequency isolated room 16 as the magnetic resonance scanner 10. In the arrangement of FIGS. 1-5, no radio frequency shield is disposed between the magnetic resonance scanner 10 and the second modality imaging system 12.

Figure 9:
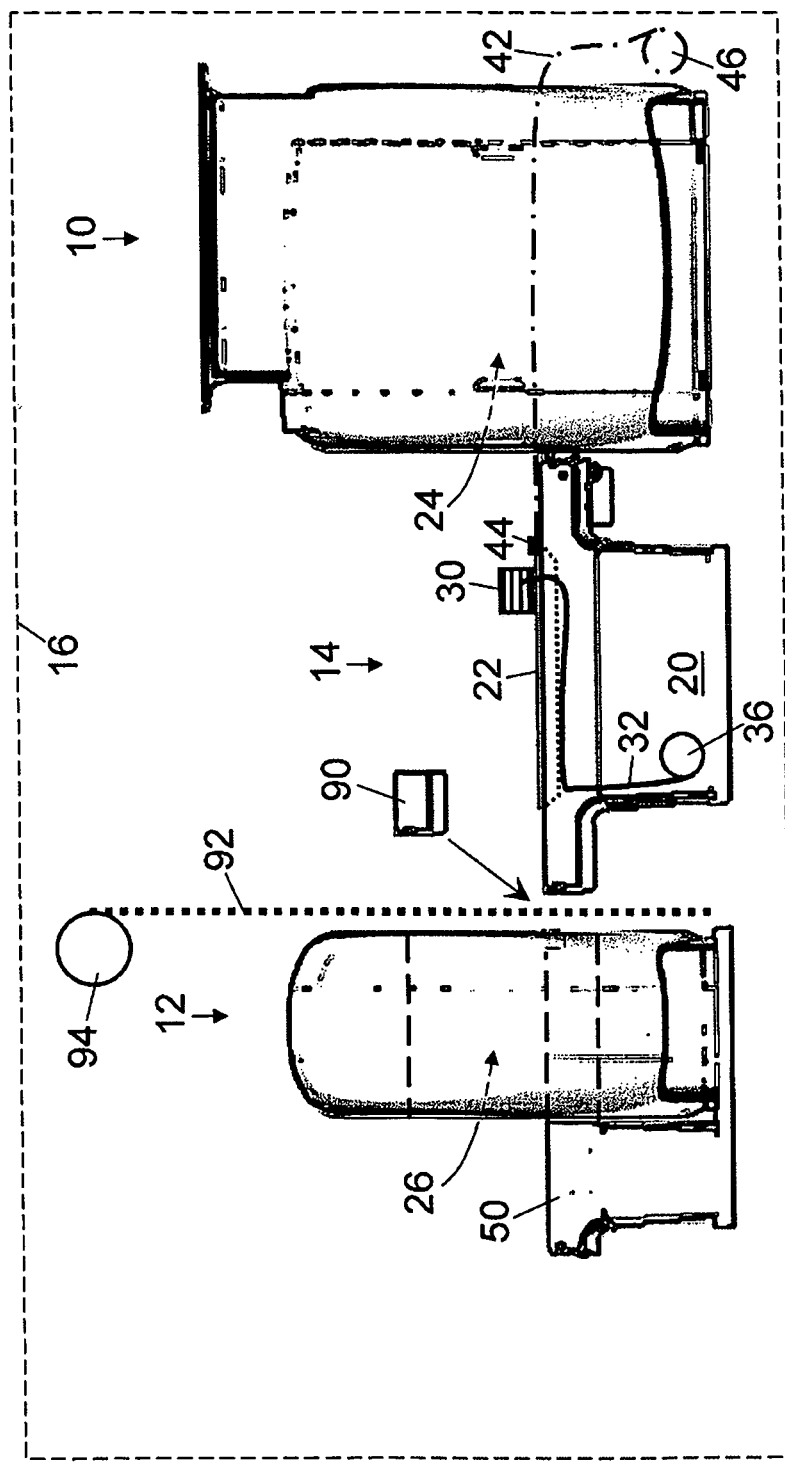
FIG. 9 diagrammatically depicts another embodiment hybrid imaging system in which a retractable radio frequency screen is selectively extendible into a gap between the magnetic resonance scanner and the second modality imaging system.

With reference to FIG. 9, another approach for constructing a hybrid imaging system including the magnetic resonance scanner 10 and the second modality imaging system 12 in the same radio frequency isolation room 16 is described. The hybrid system of FIG. 9 includes the patient bed 14 disposed between the magnetic resonance scanner 10 and the second modality imaging system 12. However, unlike the hybrid system of FIGS. 1-5, the hybrid system of FIG. 9 does not have the second modality imaging system 12 mounted on rails. Rather, the second modality imaging system 12 is stationary, and a bridge 90 is inserted between the patient bed 14 and the patient beam 50 or other support of the second modality imaging system 12 to provide a path for the patient support pallet 22 to move between the base 20 and the examination region 26 of the second modality imaging system 12. With the bridge 90 inserted, the hybrid imaging system 12 operates substantially as the hybrid imaging system of FIGS. 1-5 in order to perform second modality imaging.

When the bridge 90 is removed (as shown in FIG. 9), there is a gap between the second modality imaging system 12 and the patient bed 14. When magnetic resonance imaging is to be performed, the bridge 90 is removed, and a retractable radio frequency screen 92 is drawn across the gap between the second modality imaging system 12 and the patient bed 14. In the illustrated embodiment, the retractable radio frequency screen 92 is wrapped around a ceiling-mounted cylindrical spool 94 in similar fashion to the arrangement of a retractable screen for an overhead projector. In other contemplated embodiments, the retractable radio frequency screen may be mounted along a wall and drawn horizontally across the gap between the second modality imaging system 12 and the patient bed 14, suspended from a ceiling track or ceiling supports. In other contemplated embodiments, the retractable radio frequency screen may be a fan-type folded self-supporting radio frequency screen that is unfolded and positioned in the gap between the second modality imaging system 12 and the patient bed 14. The radio frequency screen 92 should be flexible, or have flexible joints in the case of a fan-type arrangement, and can be made, for example, of a wire mesh, wire fibers, or other distributed conductive elements embedded in a flexible plastic sheet or other flexible matrix. Alternatively, the radio frequency screen 92 can be a thin flexible metal sheet, such as an aluminum-type foil. The retractable radio frequency screen can also be configured as sliding doors, bi-fold doors, or other retractable configurations.

The retractable radio frequency screen 92 or variations thereof can also be used in embodiments in which the second modality imaging system 12 is mounted on the rails 28, or in which the magnetic resonance is performed with the second modality imaging system 12 in the less proximate (i.e., more remote) position illustrated in FIG. 2. If the gap is small enough, it is also contemplated to omit the bridge 90 and have the pallet 22 pass over the gap (which may be just slightly wider than the width of the radio frequency screen 92) without a bridge. Moreover, while in the illustrated embodiment the retractable radio frequency screen 92 is drawn between the second modality imaging system 12 and the patient bed 14, in other contemplated embodiments there is a gap between the patient bed and the magnetic resonance scanner, and the retractable radio frequency screen is drawn between the magnetic resonance scanner and the patient support. In yet other contemplated embodiments, there is no gap and instead the retractable radio frequency screen has a cut-out sized to accommodate the patient bed. The radio frequency screen 92 can be moved into position manually, or automatically based on the position of the second modality imaging system 12, removal of the bridge 90, initiation of a process operation of the magnetic resonance imaging sequence, or other suitable triggering mechanism.

In some embodiments, the retractable radio frequency screen 92 includes a ferromagnetic wire mesh, ferromagnetic fibers, mu-metal particles, or other distributed magnetic material such that the radio frequency screen also provides magnetic isolation of the second modality imaging system 12 from the static magnetic field generated by the magnetic resonance scanner. In this case, the screen 92 is moved into place during second modality imaging as well as during magnetic resonance imaging.

An advantage of the hybrid systems disclosed herein is compactness. By arranging the patient bed 14 between the imaging systems 10, 12 and implementing the approaches disclosed herein to mitigate detrimental interactions between the imaging systems 10, 12, the hybrid system is readily constructed to fit inside a typical radio frequency isolated room of the type used for containing magnetic resonance scanners. Some such typical radio frequency isolation rooms have a floor area of about 7×9 meters. In this arrangement, the second modality imaging system 12 is spaced apart from the magnetic resonance scanner 10 by a gap of less than seven meters, and more preferably by a gap of less than four meters which is sufficient to insert the patient bed 14.

In a typical arrangement, the linearly translatable patient support pallet 22 has a length of about two meters along the direction of linear translation, so as to accommodate a human patient. A linear translation range of the linearly translatable pallet 22 is suitably made less than five times a length of the patient support pallet along the direction of linear translation, and more preferably is suitably made less than four times the length of the patient support pallet 22. For maximum compactness, the range of linear translation can be made about three times the length of the patent support pallet 22: one pallet length accommodating the patient loading position of the patient support pallet 22 on the base 20; one pallet length accommodating movement of the patient support pallet 22 into the magnetic resonance scanner bore; and one pallet length accommodating movement of the patient support pallet 22 the second modality imaging system.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A patient bed comprising:
   a linearly translatable patient support pallet aligned to be selectively moved into an examination region of the magnetic resonance scanner for magnetic resonance imaging and into an examination region of the second modality imaging system for second modality imaging, a linear translation range of the linearly translatable pallet being less than five times a length of the patient support pallet along the direction of linear translation;
   a radio frequency device or device port disposed with the pallet; and
   a radio frequency cable having a first end coupled with the radio frequency device or device port.

2. The patient bed as set forth in claim 1, wherein the base includes:
   a height adjustment enabling a height of the patient support pallet to be adjusted at least when the patient support pallet is disposed between the magnetic resonance scanner and the second modality imaging system.

3. The patient bed as set forth in claim 1, wherein the linear translation range of the linearly translatable pallet is less than or about four times the length of the patient support pallet along the direction of linear translation.

4. A patient bed as set forth in claim 1, wherein the second modality imaging system is mounted to translate relative to the base parallel to the direction of linear translation of the linearly translatable patient support pallet.

5. The patient bed as set forth in claim 1, further including:
   a tensioner configured to take up slack of the radio frequency cable.

6. The patient bed as set forth in claim 1, wherein the radio frequency device or device port includes:
   a radio frequency coil or a port for connecting a radio frequency coil.

7. The patient bed as set forth in claim 1, further including:
   a dockable connection or automatic disconnect that at least disconnects the first end of the radio frequency cable from the radio frequency device or device port responsive to the patient support pallet being moved a sufficient distance toward the examination region of the second modality imaging system.

8. The patient bed as set forth in claim 1, wherein the radio frequency cable passes underneath the linearly translatable patient support pallet and to have its first end remain coupled with the radio frequency device or device port both when the patient support pallet is moved into the examination region of the magnetic resonance scanner and also when the patient support pallet is moved into the examination region of the second modality imaging system.

9. A patient bed comprising:
   a base disposed between a magnetic resonance scanner and a second modality imaging system, the second modality being other than magnetic resonance;
   a translatable patient support pallet supported by the base and aligned to be selectively moved into an examination region of the magnetic resonance scanner for magnetic resonance imaging and into an examination region of the second modality imaging system for second modality imaging;
   a radio frequency device or device port disposed with the pallet; and
   a radio frequency cable having a first end coupled with the radio frequency device or device port.

10. The patient bed as set forth in claim 9, further including:
- a tensioner configured to take up slack of the radio frequency cable.

11. The patient bed as set forth in claim 9, further including:
- an automatic disconnect that disconnects the first end of the radio frequency cable from the radio frequency device or device port responsive to the patient support pallet being moved a sufficient distance toward the examination region of the second modality imaging system.

12. The patient bed as set forth in claim 9, wherein the radio frequency cable passes underneath the linearly translatable patient support pallet and to have its first end remain coupled with the radio frequency device or device port both when the patient support pallet is moved into the examination region of the magnetic resonance scanner and also when the patient support pallet is moved into the examination region of the second modality imaging system.

13. The patient bed as set forth in claim 9, wherein the support pallet is movable from one of the examination regions into the other of the examination regions by moving the pallet a total distance of less than five times a length of the pallet.

14. The patient bed as set forth in claim 9, wherein the base comprises a stationary base including a height adjustment enabling a height of the patient support pallet to be adjusted at least when the patient support pallet is disposed between the magnetic resonance scanner and the second modality imaging system.

15. The patient bed as set forth in claim 9 wherein the translatable patient support pallet is supported between the magnetic resonance scanner and the second modality imaging system without passing through an intervening wall.

* * * * *